United States Patent
Kakinuma et al.

(10) Patent No.: US 10,575,572 B2
(45) Date of Patent: Mar. 3, 2020

(54) TRANSPARENT FILM FOR FACE PROTECTION SHIELD

(71) Applicant: DEXERIALS CORPORATION, Tokyo (JP)

(72) Inventors: Masayasu Kakinuma, Tokyo (JP); Kimitaka Nishimura, Tokyo (JP); Satoshi Kawamura, Tokyo (JP); Hideki Terashima, Tokyo (JP); Eiji Ohta, Tokyo (JP); Shunichi Kajiya, Tokyo (JP); Jun Sasaki, Tokyo (JP); Kiyoaki Tanifuji, Tokyo (JP)

(73) Assignee: DEXERIALS CORPORATION, Tokyo (JP)

( * ) Notice: Subject to any disclaimer, the term of this patent is extended or adjusted under 35 U.S.C. 154(b) by 220 days.

(21) Appl. No.: 15/328,335

(22) PCT Filed: May 27, 2015

(86) PCT No.: PCT/JP2015/065283
§ 371 (c)(1),
(2) Date: Jan. 23, 2017

(87) PCT Pub. No.: WO2016/013290
PCT Pub. Date: Jan. 28, 2016

(65) Prior Publication Data
US 2017/0208878 A1    Jul. 27, 2017

(30) Foreign Application Priority Data

Jul. 23, 2014 (JP) .................. 2014-150264
Aug. 5, 2014 (JP) .................. 2014-159228

(51) Int. Cl.
*A41D 13/11*    (2006.01)
*B32B 7/02*    (2019.01)
(Continued)

(52) U.S. Cl.
CPC ............ *A41D 13/1184* (2013.01); *A61F 9/02* (2013.01); *A61F 9/04* (2013.01); *A61F 9/045* (2013.01);
(Continued)

(58) Field of Classification Search
CPC .. A41D 13/1184; G02B 1/18; G02B 27/0006; G02B 1/04; G02B 1/118; A61F 9/02;
(Continued)

(56) References Cited

U.S. PATENT DOCUMENTS

| 5,446,925 A | 9/1995 | Baker et al. |
| 6,026,511 A | 2/2000 | Baumann et al. |

(Continued)

FOREIGN PATENT DOCUMENTS

| JP | 07-178117 | 7/1995 |
| JP | 08-197670 | 8/1996 |

(Continued)

OTHER PUBLICATIONS

Feb. 7, 2018, European Search Report issued for related EP application No. 15825390.6.
(Continued)

*Primary Examiner* — Nathan L Van Sell
(74) *Attorney, Agent, or Firm* — Paratus Law Group, PLLC

(57) ABSTRACT

There is provided a transparent film for a face protection shield in which transparency is enhanced and visibility from a non-wearer is also enhanced, the transparent film for a face protection shield including: a transparent base material having flexibility; and a transparent resin layer configured to be laminated on at least one of surfaces of the transparent base material, the transparent resin layer having on a surface a plurality of structural bodies including concavities or convexities provided at a pitch of less than or equal to a visible light wavelength. A refractive index of the transparent base material is different from a refractive index of the transparent resin layer, and an interface between the transparent base material and the transparent resin layer has a concave-convex shape.

11 Claims, 11 Drawing Sheets

(51) Int. Cl.
  *G02B 1/118* (2015.01)
  *A61F 9/04* (2006.01)
  *G02B 1/18* (2015.01)
  *G02B 27/00* (2006.01)
  *A61F 9/02* (2006.01)
  *G02B 1/04* (2006.01)

(52) U.S. Cl.
  CPC ............ *B32B 7/02* (2013.01); *G02B 1/04* (2013.01); *G02B 1/118* (2013.01); *G02B 1/18* (2015.01); *G02B 27/0006* (2013.01); *B32B 2551/00* (2013.01)

(58) Field of Classification Search
  CPC ... A61F 9/045; A61F 9/04; B32B 7/02; B32B 2551/00
  See application file for complete search history.

(56) References Cited

U.S. PATENT DOCUMENTS

| | | |
|---|---|---|
| 2005/0133035 A1 | 6/2005 | Yahiaoui et al. |
| 2009/0046379 A1 | 2/2009 | Kuramoto et al. |
| 2010/0238548 A1* | 9/2010 | Watanabe ............... G02B 1/04 359/488.01 |
| 2011/0002041 A1 | 1/2011 | Tazawa |
| 2012/0088106 A1* | 4/2012 | Jing ..................... B82Y 30/00 428/426 |
| 2012/0243097 A1 | 9/2012 | Hayashibe et al. |
| 2013/0302564 A1* | 11/2013 | Takihara ............ C08F 290/046 428/141 |
| 2014/0272295 A1* | 9/2014 | Deshpande ............. G02B 1/12 428/142 |
| 2015/0231854 A1 | 8/2015 | Nakai et al. |

FOREIGN PATENT DOCUMENTS

| | | |
|---|---|---|
| JP | 2001-525203 | 12/2001 |
| JP | 2008-158293 | 7/2008 |
| JP | 2010-202881 | 9/2010 |
| JP | 2011-028229 | 2/2011 |
| JP | 2012-203018 | 10/2012 |
| JP | 2014-041206 | 3/2014 |
| WO | WO2006-121102 | 11/2006 |
| WO | WO 2014/065136 A1 | 5/2014 |

OTHER PUBLICATIONS

Apr. 1, 2019, Taiwanese Office Action issued for related TW Application No. 104116999.

* cited by examiner

TRANSPARENT FILM FOR FACE PROTECTION SHIELD

CROSS REFERENCE TO PRIOR APPLICATION

This application is a National Stage Patent Application of PCT International Patent Application No. PCT/JP2015/065283 (filed on May 27, 2015) under 35 U.S.C. § 371, which claims priority to Japanese Patent Application Nos. 2014-150264 (filed on Jul. 23, 2014) and 2014-159228 (filed on Aug. 5, 2014), which are all hereby incorporated by reference in their entirety.

TECHNICAL FIELD

The present technology relates to a transparent film used for a face protection shield which protects a face of a wearer from splashed matters and flying fragments, and also ensures a field of view that is necessary for the wearer.

BACKGROUND ART

Masks with eye shields have widely been used conventionally in surgical operations and the like. For example, Patent Literature 1 discloses a face shield mask having a structure in which a transparent plastic film serving as an eye shield is attached to a face mask.

In the above-mentioned eye shield, since the refractive index of the transparent plastic film having flexibility is generally more than or equal to 1.3, light reflects on the interface between the plastic film and the air. For example, the plastic film serving as an eye shield described in Patent Literature 1 is made of polyethylene terephthalate having a refractive index of 1.58. Accordingly, the reflectance of light on the interface between the eye shield and the air is 5.05%, for example, and, taking into account the reflection at the back and front of the eye shield, 10.1% of incident light in total is reflected light. Therefore, in an operating room in which a light with extremely high light intensity (for example, illuminance of more than or equal to 140000 lux) is used, the intensity of the reflected light also increases.

Accordingly, for example, Patent Literature 2 discloses a coating composition that is suitable to be served as a coating on a surface of a surgical face shield used under a surgical light having a high light intensity, and is capable of imparting anti-reflection properties and anti-fogging properties to a surface of a transparent or translucent base material. Further, Patent Literature 2 discloses that a light transmittance of a film coated with the coating composition disclosed in Patent Literature 2 is increased by 11 to 11.2% with respect to a light transmittance of a non-coated film.

| Patent Literature | Citation List |
| --- | --- |
| Patent Literature 1: | JP H7-178117A |
| Patent Literature 2: | JP 2010-202881A |

SUMMARY OF INVENTION

Technical Problem

However, the light transmittance of the film coated with the coating composition disclosed in Patent Literature 2 with respect to light having a wavelength of 550 nm is approximately 97.0%, and there is still the reflected light of nearly 3%.

Therefore, in order to be used as a face protection shield such as an eye shield or a face shield, the anti-reflection properties of the film coated with the coating composition disclosed in Patent Literature 2 are not sufficient.

On the other hand, in the case where the anti-reflection properties of the transparent film used for the face protection shield are remarkably enhanced, since it becomes difficult to visually recognize the presence of the transparent film, easy handleability of the transparent film in producing the face protection shield deteriorates. Further, in the case where a wearer wears the face protection shield, since it becomes difficult for a non-wearer to visually recognize presence or absence of wearing of the face protection shield, convenience in performing safety check deteriorates. Still further, in performing a surgical operation or the like, in the case where a non-wearer wipes sweat on a face of a wearer who wears the face protection shield, since it is difficult for the non-wearer to visually recognize presence or absence of the face protection shield, it is difficult to perform an action of wiping sweat.

Accordingly, the present invention has been devised in light of the above issue, and an object of the present invention is to provide a novel and improved transparent film for a face protection shield in which transparency is enhanced and visibility from a non-wearer is also enhanced.

Solution to Problem

According to an aspect of the present invention in order to solve the above-mentioned problem, there is provided a transparent film for a face protection shield including: a transparent base material having flexibility; and a transparent resin layer configured to be laminated on at least one of surfaces of the transparent base material, the transparent resin layer having on a surface a plurality of structural bodies including concavities or convexities provided at a pitch of less than or equal to a visible light wavelength. A refractive index of the transparent base material is different from a refractive index of the transparent resin layer, and an interface between the transparent base material and the transparent resin layer has a concave-convex shape.

A difference between the refractive index of the transparent base material with respect to light having a wavelength of 589 nm and the refractive index of the transparent resin layer with respect to light having a wavelength of 589 nm may be more than or equal to 0.05.

The concave-convex shape may have a height difference in a range of 0.1 to 9.5 μm and a pitch in a range of 1 to 100 mm.

Each of both sides of the transparent base material may be laminated with the transparent resin layer.

The transparent resin layer may be a cured product of an ultraviolet-curing resin composition having a hydrophilic functional group.

According to another aspect of the present invention in order to achieve the above-mentioned object, there is provided a face protection shield to which the above-mentioned transparent film for a face protection shield is attached.

Advantageous Effects of Invention

As described above, according to the present invention, there is provided the transparent film for a face protection shield in which transparency is enhanced and visibility from a non-wearer is also enhanced. Thus, the face protection shield to which the present invention is applied can ensure a remarkably bright field of view for the wearer, and can be recognized easily by the non-wearer presence or absence of wearing.

DESCRIPTION OF EMBODIMENTS

Figure 1:
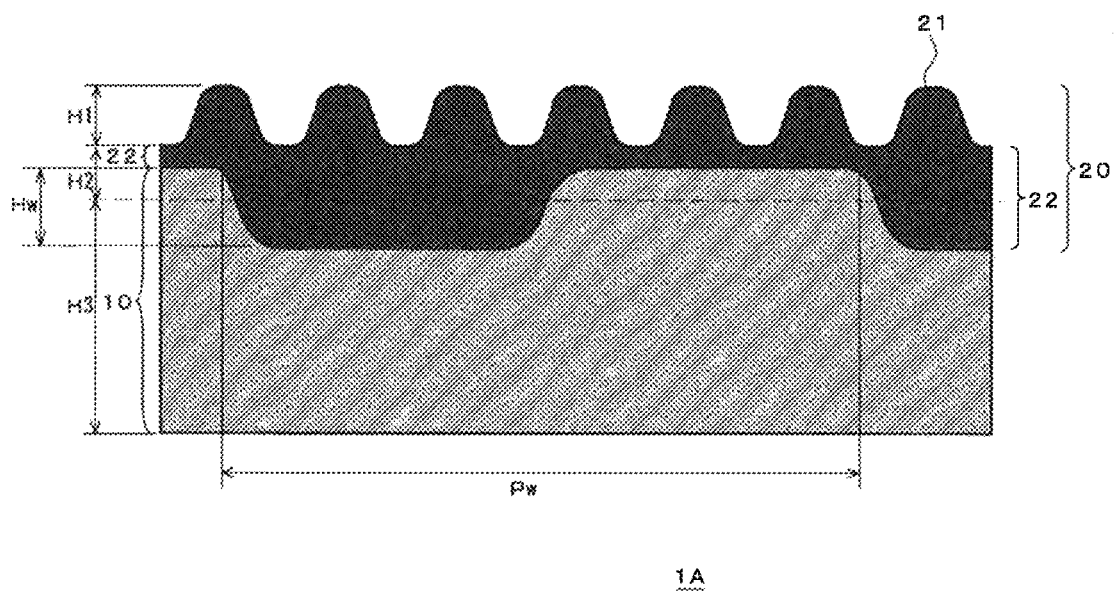
FIG. 1 is a cross-sectional view in a thickness direction of a transparent film according to an embodiment of the present invention.

Hereinafter, (a) preferred embodiment(s) of the present invention will be described in detail with reference to the appended drawings. In this specification and the appended drawings, structural elements that have substantially the same function and structure are denoted with the same reference numerals, and repeated explanation of these structural elements is omitted.

Note that, in the present description, being "transparent" means that, in the visible light band (to be specific, 360 nm to 830 nm), for example, approximately more than or equal to 70% of incident light is transmitted and light absorption is approximately less than 30% of the incident light.

<1. Transparent Film for Face Protection Shield>
<1.1. Overview>

Figure 2:
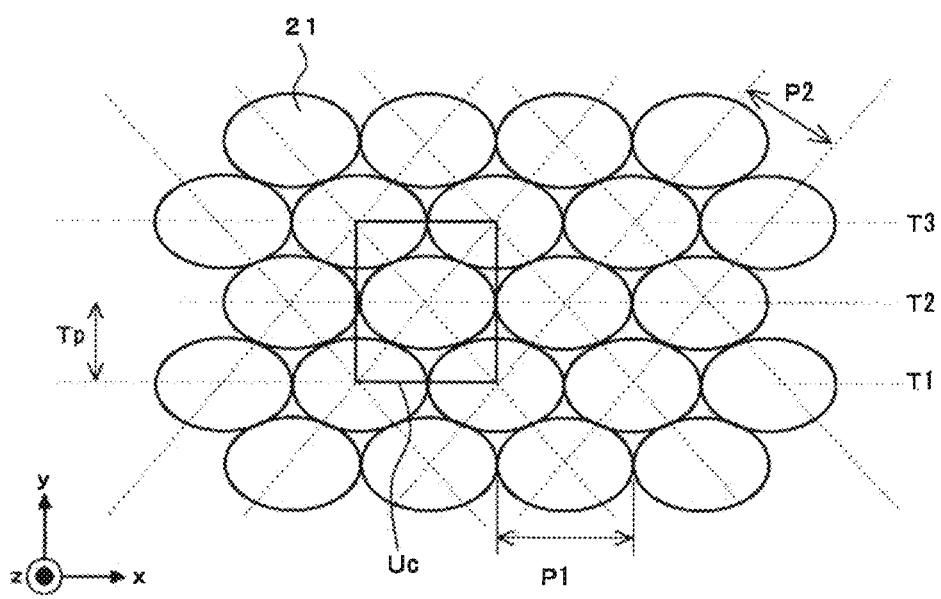
FIG. 2 is a plan view viewing the transparent film according to the embodiment in a direction perpendicular to a film surface.

First, with reference to FIG. 1 and FIG. 2, a transparent film for a face protection shield (hereinafter, may also be simply referred to as "transparent film") according to an embodiment of the present invention will be described. FIG. 1 is a cross-sectional view schematically showing a cross-section in a thickness direction of a transparent film 1A for a face protection shield according to an embodiment of the present invention, and FIG. 2 is a schematic plan view viewing the transparent film 1A for a face protection shield in a direction perpendicular to a film surface.

As shown in FIG. 1, the transparent film 1A according to the present embodiment has a structure in which a transparent base material 10 having flexibility and a transparent resin layer 20 are laminated, the transparent resin layer 20 having multiple structural bodies (so-called moth-eye structure) including concavities or convexities provided at a pitch of less than or equal to the visible light wavelengths. Note that, in the case where the transparent film 1A is used for a face protection shield, the back and front of the transparent film 1A does not have to be taken into account. To be specific, the face protection shield may be formed in a manner that the surface on which the transparent base material 10 of the transparent film 1A is provided faces a wearer or may also be formed in a manner that the surface on which the transparent resin layer 20 is provided faces the wearer.

Further, a refractive index of the transparent base material 10 is different from a refractive index of the transparent resin layer 20, and the interface between the transparent base material 10 and the transparent resin layer 20 has a concave-convex shape (which can also be said that the interface between the transparent base material 10 and the transparent resin layer 20 has undulations). Note that the shape of the interface between the transparent base material 10 and the transparent resin layer 20 can be observed at a section obtained by cutting the transparent film 1A in any direction on a surface perpendicular to the film surface, for example.

The transparent film 1A according to the present embodiment enhances the anti-reflection properties by forming the multiple structural bodies (so-called moth-eye structure) including concavities or convexities provided at a pitch of less than or equal to the visible light wavelengths on a surface of the transparent resin layer 20. Further, the transparent film 1A according to the present embodiment forms a rainbow-colored reflection pattern on the transparent film 1A, which can only be observed by a non-wearer, by causing the refractive index of the transparent base material 10 to be different from the refractive index of the transparent resin layer 20, and by providing the interface between the transparent base material 10 and the transparent resin layer 20 with the concave-convex shape. With such structures, transparency of the transparent film 1A for a face protection shield can be further enhanced and visibility from a non-wearer can be enhanced.

<1.2. Configurations of Transparent Film>
(Transparent Resin Layer)

The transparent resin layer 20 includes multiple structural bodies 21 (moth-eye structure) which includes multiple concavities or convexities provided two-dimensionally at a pitch of less than or equal to the visible light wavelengths, and a basal layer 22 which supports individual structural bodies 21 and is formed integrally with the structural bodies 21. With such a moth-eye structure, the transparent resin layer 20 can be imparted with anti-reflection properties.

The multiple structural bodies 21 included in the moth-eye structure are each a structural body which forms a convexity or a concavity with respect to the film surface of the transparent film 1A. The three-dimensional shape of the structural body 21 may be any, and, for example, may be a bell shape or a truncated elliptical cone shape. Further, the planar shape of the structural body 21 viewed in the direction perpendicular to the film surface may also be any, and, for example, may be a circle or an ellipse.

Further, a height H1 of the structural body 21 is preferably more than or equal to 180 nm and less than or equal to 300 nm, more preferably more than or equal to 190 nm and less than or equal to 300 nm, and still more preferably more than or equal to 190 nm and less than or equal to 230 nm. In the case where the height of the structural body 21 has a value within such a range, the anti-reflection properties of the transparent film 1A can be further enhanced. Further, as will be described later, in the case where the moth-eye structure of the transparent resin layer 20 is formed by a transfer method, releasability in the event of releasing the transparent resin layer 20 from a mold after the transfer can be enhanced. Note that the heights of the structural bodies 21 may be different from each other.

An arrangement pattern of the multiple structural bodies 21 included in the moth-eye structure is, as shown in FIG. 2 for example, a pattern in which tracks T1, T2, T3 each having structural bodies 21 arranged in the X direction are arranged alternately in the Y direction. In FIG. 2, P1 represents a pitch (hereinafter, also referred to as dot pitch) of structural bodies 21 in a track in the X direction, P2 represents a pitch of structural bodies 21 between adjacent tracks, and TP represents a pitch (hereinafter, referred to as track pitch) of tracks. Moreover, UC represents a unit lattice in the arrangement pattern shown in FIG. 2.

Here, the dot pitch P1 within a track of structural bodies 21 and the pitch P2 between tracks are set so as to be less than or equal to the visible light wavelengths in order to achieve anti-reflection properties. For example, P1 and P2 may each be 100 nm to 830 nm.

Further, regarding the arrangement pattern of the structural bodies 21 shown in FIG. 2, in adjacent tracks T1, T2, and T3, a position of a structural body 21 is offset by half the dot pitch P1 for each track. In this manner, regarding the arrangement pattern of the structural bodies 21 shown in FIG. 2, the structural bodies 21 are arranged in a hexagonal lattice shape.

Note that, in the present invention, the arrangement pattern of the structural bodies 21 is not limited to the hexagonal lattice shape shown in FIG. 2. The arrangement pattern of the structural bodies 21 may be any two-dimensional pattern, and, for example, may be a tetragonal lattice shape or a random shape.

A filling factor (average filling factor) of the structural bodies 21 in planar viewing of the transparent resin layer 20 is, with 100% as the upper limited, preferably more than or equal to 40%, more preferably more than or equal to 65%, still more preferably more than or equal to 73%, and most preferably more than or equal to 86%. With the filling factor of the structural bodies 21 in the above range, the anti-reflection properties can be further enhanced.

Here, the filling factor of the structural bodies 21 can be determined as follows.

First, a surface of the transparent resin layer 20 is photographed in a direction perpendicular to the film surface of the transparent film 1A using a scanning electron microscope (SEM). Next, a unit lattice UC of the arrangement pattern is selected randomly from the SEM photograph that has been taken, and, in order to calculate each side of the unit lattice UC, the dot pitch P1 and the track pitch TP of the structural bodies 21 are measured. Subsequently, an area $S_{UNIT}$ of the unit lattice is calculated from the measured dot pitch P1 and track pitch TP. Note that, in the case where the arrangement pattern of the structural bodies 21 is in a hexagonal lattice shape or a quasi-hexagonal lattice shape, $S_{UNIT}$ can be calculated by P1×2TP. Further, an area $S_{DOT}$ of the base of the structural body 21 placed at the center of the unit lattice UC is measured through image processing. Using those measurement results, the filling factor can be determined from the following equation.

Filling factor=$(S_{DOT}/S_{UNIT})\times 100$

The calculation of the filling factor described above is performed for multiple (for example, ten) unit lattices selected randomly from the SEM photograph that has been taken, the average of the calculated filling factors is calculated, and thus, the filling factor of the structural bodies 21 can be determined.

Note that, as a method of increasing the filling factor, there is given, for example, bonding together the lower portions of adjacent structural bodies 21, or decreasing an area of a non-structural body part in planar viewing of the transparent resin layer 20 by adjusting the shapes of the bases of the structural bodies 21.

The basal layer 22 is formed integrally with the structural bodies 21 and supports individual structural bodies 21. The thickness of the basal layer 22 changes in a corresponding manner to the concave-convex shape of the interface between the transparent base material 10 and the transparent resin layer 20. An average thickness H2 of the basal layer 22 is preferably 0.5 to 10 μm, and more preferably 0.5 to 7 μm.

Note that the average thickness H2 of the basal layer 22 can be determined by calculating an average film thickness through measurement of the film thickness of the transparent film 1A for multiple times (for example, ten times) using a digimatic measuring unit (Litematic VL-50S-B, manufactured by Mitutoyo Corporation), for example, and then subtracting the height H1 (design value) of the structural body 21 and a film thickness H3 of the transparent base material 10 from the calculated average film thickness. Note that, for the measurement of the average thickness H2 of the basal layer 22, the measurement is preferably performed in a direction parallel to the longest side of the film width every approximately 10% of the length of the longest side or every approximately 3 mm.

Further, the transparent resin layer 20 is made of a transparent organic resin. Further, as will be described later, in the case where a transfer method is used for forming the structural bodies 21 on the transparent resin layer 20, the transparent resin layer 20 is preferably made of a curing resin. It is more preferred that the transparent resin layer 20 have high light transmittance after curing, have a refractive index within a predetermined range to be mentioned later, and be made of a hydrophilic curing resin.

The refractive index of the curing resin that forms the transparent resin layer (measured by a sodium D line (wavelength of 589 nm)) is preferably more than or equal to 1.40 and less than or equal to 2.00, and more preferably more than or equal to 1.43 and less than or equal to 2.00. In general, a resin having a high refractive index after curing has high viscosity before the curing. Accordingly, in the case where the refractive index of the curing resin exceeds 2.00, it is difficult to form structural bodies 21 having desired shapes in the event of forming the structural bodies 21 on the surface of the transparent resin layer 20 by the transfer method, as will be described later, which is not preferable.

Further, in the case where the curing resin that forms the transparent resin layer 20 is hydrophilic, the transparent film 1A hardly fogs with moisture. Thus, when a face protection shield formed by using the transparent film 1A is worn on a face of a wearer, the transparent film 1A can be prevented from being fogged by a breath of the wearer.

As the hydrophilic curing resin, it is preferred to use an ultraviolet-curing resin having a hydrophilic functional group. Note that a case may be assumed in which a hydrophilicity is imparted to the transparent resin layer 20 by forming a hydrophilic coating film on the surface of the transparent resin layer 20. In such a case, however, since the moth-eye structure formed on the surface of the transparent resin layer is covered by the hydrophilic coating film and the anti-reflection properties may be impaired, it is not preferable.

As the curing resin that forms the transparent resin layer 20, there can be used, to be specific, an ultraviolet-curing resin obtained by polymerizing a monofunctional monomer, a bifunctional monomer, or a multifunctional monomer with a photopolymerization initiator.

Here, examples of monofunctional monomers include carboxylic acid monomers (acrylic acids and the like), hydroxy monomers (2-hydroxyethyl acrylate, 2-hydroxypropyl acrylate, 4-hydroxybutyl acrylate, and the like), alkyl or alicyclic monomers (isobutyl acrylate, t-butyl acrylate, isooctyl acrylate, lauryl acrylate, stearyl acrylate, isobornyl acrylate, cyclohexyl acrylate, and the like), other functional monomers (2-methoxyethyl acrylate, methoxyethylene glycol acrylate, 2-ethoxyethyl acrylate, tetrahydrofurfuryl acrylate, benzyl acrylate, ethyl carbitol acrylate, phenoxyethyl acrylate, N,N-dimethylamino ethyl acrylate, N,N-dimethylamino propyl acrylamide, N,N-dimethyl acrylamide, acryloyl morpholine, N-isopropyl acrylamide, N,N-diethyl acrylamide, N-vinyl pyrrolidone, 2-(perfluorooctyl)ethyl acrylate, 3-perfluorohexyl-2-hydroxypropyl acrylate, 3-perfluorooctyl-2-hydroxypropyl acrylate, 2-(perfluorodecyl) ethyl acrylate, 2-(perfluoro-3-methylbutyl)ethyl acrylate, 2,4,6-tribromophenol acrylate, 2,4,6-tribromophenol methacrylate, 2-(2,4,6-tribromophenoxy)ethyl acrylate, and 2-ethylhexyl acrylate.

Examples of bifunctional monomers include tri(propylene glycol) di-acrylate, trimethylolpropane diaryl ether, and urethane acrylate.

Examples of multifunctional monomers include trimethylolpropane tri-acrylate, dipentaerythritol pentaacrylate, dipentaerythritol hexaacrylate, and ditrimethylolpropane tetra-acylate.

Note that more preferable is a curing resin obtained by polymerizing, among the above-mentioned monofunctional monomers, bifunctional monomers, and multifunctional monomers, a monomer having a hydrophilic group such as a hydroxy group, a carboxy group, an amino group, and an amide group as described above.

As the photopolymerization initiator for polymerizing the above monomers include, there can be used, for example, 2,2-dimethoxy-1,2-diphenylethane-1-one, 1-hydroxy-cyclohexyl phenyl ketone, and 2-hydroxy-2-methyl-1-phenyl propane-1-one.

In addition thereto, fillers such as inorganic fine particles and organic fine particles may be included in a before-curing composition of the curing resin that forms the transparent resin layer 20. Examples of inorganic fine particles include metallic oxide fine particles such as $SiO_2$, $TiO_2$, $ZrO_2$, $SnO_2$, and $Al_2O_3$. Examples of organic fine particles include resin fine particles formed of a transparent organic resin.

Further, functional additives such as leveling agents, surface conditioners, and antifoaming agents may be added to the before-curing composition of the curing resin that forms the transparent resin layer 20.

(Transparent Base Material)

The transparent base material 10 is made of a flexible transparent resin, and supports the transparent resin layer 20. Further, in the transparent film 1A according to the present invention, the interface between the transparent base material 10 and the transparent resin layer 20 has a concave-convex shape. To be specific, the concave-convex shape is formed on the surface at the transparent resin layer 20 side of the transparent base material 10. Owing to the concave-convex shape, thickness unevenness can be formed on the basal layer 22 of the transparent resin layer 20, and hence, the transparent film 1A can have a reflection pattern that can only be observed by a non-wearer.

Note that the concave-convex shape represents a wave shape in which the height difference between the concavities and convexities is more than or equal to ⅓ the height of the structural body 21, and the pitch of the concavities and convexities is more than or equal to 100 times the length of the pitch of the arrangement pattern of the structural bodies 21.

A height difference Hw of the concave-convex shape is preferably determined in accordance with the average thickness of the basal layer 22. For example, in the case where the average thickness H2 of the basal layer 22 is less than 1.5 μm, the height difference Hw of the concave-convex shape is preferably 0.1 to 1 μm. Further, in the case where the average thickness H2 of the basal layer 22 is more than or equal to 1.5 μm and less than 5 μm, the height difference Hw is preferably 0.1 μm to 4.5 μm. Still further, in the case where the average thickness H2 of the basal layer 22 is more than or equal to 5 μm and less than or equal to 10 μm, the height difference Hw is preferably 0.1 to 9.5 μm.

Further, the pitch of the concave-convex shape is, in order to make the rainbow-colored reflection pattern which can only be observed by a non-wearer easier to see, preferably within the range of 1 to 100 mm, and more preferably within the range of 2.5 to 50 mm.

Note that the concave-convex shape of the interface between the transparent base material 10 and the transparent resin layer 20 is preferably formed over a large region in order to enhance the visibility of the transparent film 1A, but is not necessarily formed over an entire region.

The average thickness H3 of the transparent base material 10 is appropriately selected in accordance with the usage of the transparent film 1A. For example, in the case where a face protection shield is formed by fixing the transparent film 1A to a face mask, the average thickness H3 of the transparent base material 10 is preferably more than or equal to 10 μm and less than or equal to 500 μm, more preferably more than or equal to 50 μm and less than or equal to 500 μm, and still more preferably more than or equal to 50 μm and less than or equal to 300 μm.

In the case where the average thickness H3 of the transparent base material 10 is more than or equal to 10 μm, the face protection shield formed by using the transparent film 1A can exhibit sufficient protection performance with respect to splashed matters or flying fragments. Further, in the case where the average thickness H3 of the transparent base material 10 is less than or equal to 500 μm, the transparent film 1A can reduce weight. In addition, since the flexibility of the transparent film 1A increases and it becomes easy to deform the transparent film 1A into a curved shape, a feel when the face protection shield is fitted as a protection member can be enhanced. Note that the average thickness H3 can be measured by a known method, and for example, an average value which is determined through measurement for multiple times (for example, ten times) using a digimatic measuring unit (Litematic VL-50S-B, manufactured by Mitutoyo Corporation) can be used.

Moreover, the refractive index of the transparent base material 10 differs from the refractive index of the transparent resin layer 20. To be specific, the difference between the refractive index of the transparent base material 10 with respect to light having a wavelength of 589 nm and the refractive index of the transparent resin layer 20 with respect to light having a wavelength of 589 nm is preferably more than or equal to 0.05 and less than or equal to 0.3, and more preferably more than or equal to 0.05 and less than or equal to 0.2.

By providing a difference between the refractive index of the transparent base material 10 and the refractive index of the transparent resin layer 20, in combination with the thickness unevenness on the basal layer 22 of the transparent resin layer 20, the reflected light beams from the back and front surfaces of the basal layer 22 can be interfered with each other. To be specific, the reflected light on the interface between the layer in which the refractive index is gradually changing owing to the structural bodies 21 (that is, a layer obtained by excluding the basal layer 22 from the transparent resin layer 20) and the basal layer can be interfered with the reflected light on the interface between the transparent base material 10 and the basal layer 22. Further, the degree of interference that occurs owing to the basal layer 22 changes periodically, since the thickness of the basal layer 22 is uneven.

Consequently, a rainbow-colored reflection pattern is visually recognized on the transparent film 1A. However, the rainbow-colored reflection pattern is not visually recognized by the wearer who wears the face protection shield including the transparent film 1A. Accordingly, the transparent film 1A according to the present embodiment can provide the wearer of the face protection shield including the transparent film 1A with a bright and clear field of view, while enhancing the visibility from a non-wearer and also enhancing the handleability.

As materials for forming the above-mentioned transparent base material 10, there may be used various known transparent resins each having a refractive index different from the refractive index of the transparent resin layer 20, for example. To be specific, examples of materials for forming the transparent base material 10 include polyethylene terephthalate (PET), polycarbonate (PC), methyl methacrylate polymer, styrene polymer, methyl methacrylate copolymer, styrene copolymer, methyl methacrylate-styrene copolymer, cellulose diacetate, cellulose triacetate, cellulose acetate butyrate, polyester, polyamide, polyimide, polyether sulfone, polysulfone, polypropylene, polymethylpentene, polychlorovinyl, polyvinyl acetal, polyether ketone, polyurethane, cycloolefin polymer, and cycloolefin copolymer (COC). Further, in the case where heat resistance is taken into account, an aramid resin may be used as a material for forming the transparent base material 10. Moreover, thin film glass having flexibility can also be used as a material for forming the transparent base material 10.

As described above, the transparent film 1A for a face protection shield according to the present invention includes, on the surface of the transparent base material 10, the transparent resin layer 20 having multiple structural bodies 21 including concavities or convexities provided at a pitch of less than or equal to the visible light wavelengths. Consequently, the transparent film 1A according to the present invention can reduce the reflected light even under a light with extremely high intensity, and can allow the light transmittance with respect to light having a wavelength of 550 nm to be more than or equal to 98.5%.

Further, since the interface between the transparent base material 10 and the transparent resin layer 20 of the transparent film 1A according to the present invention has the concave-convex shape, the thickness of the basal layer 22 that supports the structural bodies 21 changes, and the refractive index of the transparent base material 10 differs from the refractive index of the transparent resin layer 20. Consequently, in the transparent film 1A according to the present invention, reflected lights interfere owing to the basal layer 22, and the rainbow-colored reflection pattern can be observed. The reflection pattern is only observed by a non-wearer of the face protection shield including the transparent film 1A, and is not observed by the wearer, and therefore, the transparent film 1A can ensure the field of view of the wearer while enhancing the visibility from the non-wearer.

Note that, in the transparent film 1A for a face protection shield, in order to enhance the visibility from the non-wearer, it is also possible to attach a frame to the transparent film 1A or provide the transparent film 1A with printing partially, however, in such cases, manufacturing cost may increase.

On the other hand, the concave-convex shape on the surface of the transparent base material 10 of the transparent film 1A according to the present invention can be formed at low cost by using a nip roller having a concave-convex shape on the surface thereof in the event of manufacturing a film to be used as the transparent base material 10 or by performing surface treatment on the transparent base material 10, for example. Accordingly, the transparent film 1A according to the present invention can also suppress increase in the manufacturing cost.

<1.3. Method of Manufacturing Transparent Film>

Regarding a method of manufacturing the transparent film 1A, for example, the transparent resin layer 20 is formed on the transparent base material 10 that has the concave-convex shape on the surface, the structural bodies 21 are formed on the transparent resin layer 20 by the transfer method or the like, and thus, the transparent film 1A can be manufactured.

To be specific, first, a resin sheet to be used as the transparent base material is prepared. On the surface of the resin sheet, a concave-convex shape is formed by using a nip roller having a concave-convex shape in the event of molding, for example.

Next, an uncured ultraviolet-curing resin composition is applied to the surface of the resin sheet on which the concave-convex shape is formed, the applied surface is put into close contact with a master on which the moth-eye structure is formed, and after that, the ultraviolet-curing resin composition is cured by being irradiated with ultraviolet rays and the like. Subsequently, after the ultraviolet-curing resin composition has been cured, the resin sheet is separated from the master, and thus, the transparent film 1A can be manufactured. Note that the ultraviolet-curing resin composition is a mixture of an ultraviolet-curing resin, a photopolymerization initiator, and additionally a filler, an additive, and the like.

Further, the master on which the moth-eye structure is formed can be manufactured by the following method. To be specific, as described in WO 2012/133943, first, a resist is applied to a roll-shaped glass master, then patterning is performed by photolithography using laser light, and a master having a fine concave-convex pattern (moth-eye structure) formed on the surface may be manufactured. Alternatively, as described in JP 2011-053496A, an anodic oxidized porous alumina substrate obtained by subjecting an aluminum substrate to anodic oxidation may be used as the master.

<1.4. Modified Example of Transparent Film>

Figure 3:
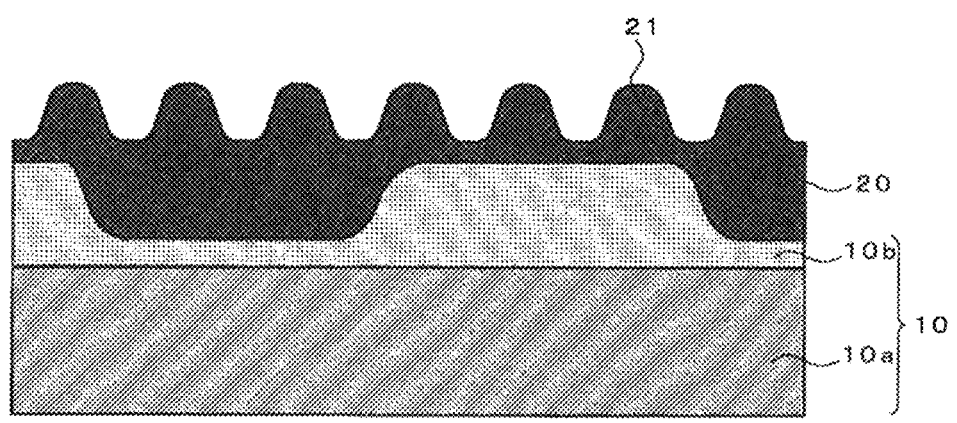
FIG. 3 is a cross-sectional view in a thickness direction of a transparent film according to a first modified example.
Figure 4:
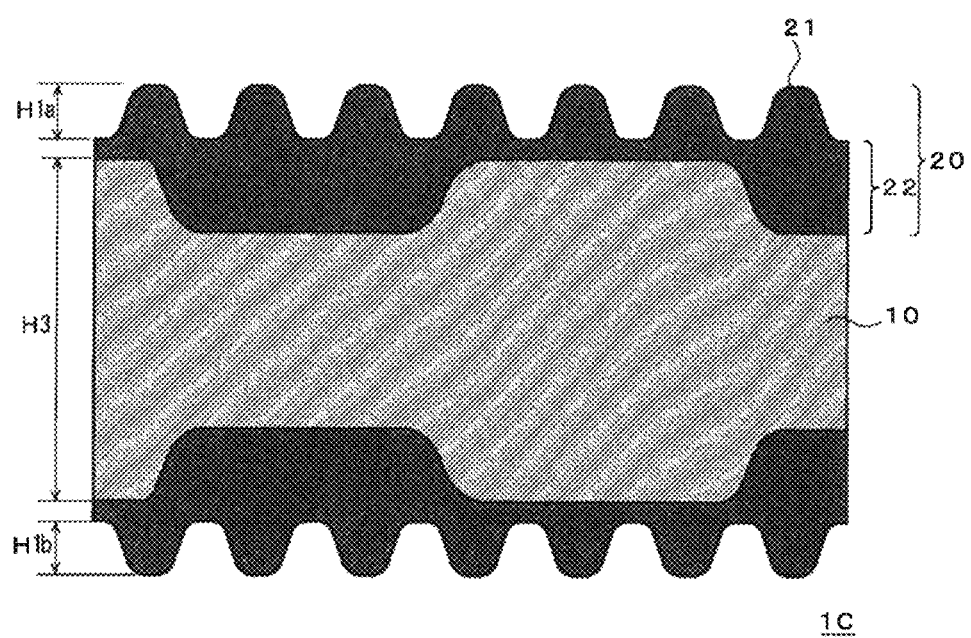
FIG. 4 is an example of a cross-sectional view in a thickness direction of a transparent film according to a second modified example.
Figure 5:
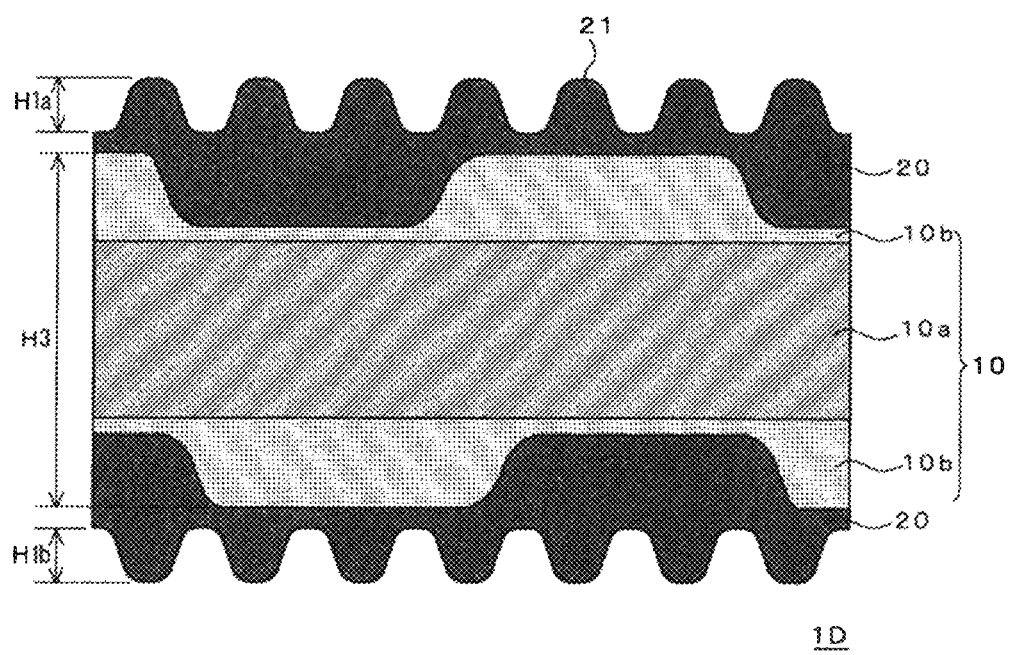
FIG. 5 is another example of the cross-sectional view in the thickness direction of the transparent film according to the second modified example.

Subsequently, with reference to FIGS. 3 to 5, various modified examples of the transparent film according to the present embodiment will be described. FIG. 3 is a cross-sectional view schematically showing a cross section in a thickness direction of a transparent film according to a first modified example of the present embodiment. FIGS. 4 and 5 are each a cross-sectional view schematically showing a cross section in a thickness direction of a transparent film according to a second modified example of the present embodiment.

First Modified Example

In the first modified example, as shown in FIG. 3, a transparent film 1B includes a transparent resin sheet 10a in which the back and front are flat, a surface treatment layer 10b which is provided on one surface of the transparent resin sheet 10a, and a transparent resin layer 20 which is formed on the surface treatment layer 10b. Further, on the surface at the transparent resin layer 20 side of the surface treatment layer 10b, a concave-convex shape is formed.

Such a surface treatment layer 10b functions as an anchor coat layer or a primer layer for increasing adhesiveness between the transparent resin sheet 10a and the transparent resin layer 20. The surface treatment layer 10b may be formed as a coating layer made of, for example, an organo-alkoxy metal compound, polyester, acrylic modified polyester, or polyurethane.

Note that, in order to form a predetermined concave-convex shape on the surface of the surface treatment layer 10b, the surface treatment layer 10b may be coated using a coating roll having a concave-convex shape on the surface, for example.

Second Modified Example

In a second modified example, as shown in FIGS. 4 and 5, the both surfaces of the transparent base material 10 are each provided with a transparent resin layer 20. In such a case, at least one interface between the transparent base material 10 and the transparent resin layer 20 may have a concave-convex shape.

For example, in a transparent film 1C shown in FIG. 4, the both surfaces of the transparent base material 10 are each provided with the transparent resin layer 20. Further, in a transparent film 1D shown in FIG. 5, the both surfaces of the transparent base material 10 are each provided with the transparent resin layer 20 via a surface treatment layer 10b.

With the both surfaces of the transparent base material 10 each being provided with the transparent resin layer 20, the reflected light can be suppressed even under a surgical light or the like with extremely high illuminance, and the light transmittances of the transparent films 1C and 1D can each be set to more than or equal to 99%. In such transparent films 1C and 1D with extremely high transparency, it is particularly important, in order to enhance visibility and handleability, to make the interface between the transparent base material 10 and the transparent resin layer 20 the concave-convex shape and to allow the rainbow-colored reflection pattern to be observed.

Note that, in the transparent resin layers 20 on the both sides of the transparent base material 10, the structural bodies 21 formed on each transparent resin layer 20 are not necessarily the same in shape, height, pitch, and the like, and may be different from each other.

Note that, where a height of the structural bodies 21 of the transparent resin layer 20 provided on one surface of the transparent base material 10 is represented by H1a, an average thickness of the transparent base material 10 is represented by H3, and a height of the structural bodies 21 provided on the other surface of the transparent base material 10 is represented by H1b, in order to fix a shield material in the face protection shield and to obtain a stable field of view without distortion, H1a:H3:H1b is preferably 18 to 30:800 to 300000:18 to 30, and is more preferably 18 to 30:1000 to 50000:18 to 30.

<2. Face Protection Shield>

Next, with reference to FIGS. 6 and 7, the face protection shield including the transparent film according to the present invention will be described. The face protection shield is, for example, a transparent shield material of a goggle type, a face mask type, a sun visor type, or the like which is used by a medical worker or the like for protecting his/her face. Such a face protection shield can be obtained by fixing or attaching in a detachable manner the transparent film according to the present invention to the face mask or the like. Note that a target to which the transparent film according to the present invention is attached is not limited to the face mask. For example, the transparent film according to the present invention may be attached to a head covering of a sun visor type, and the target can be selected appropriately in accordance with the form of the face protection shield.

Figure 6:
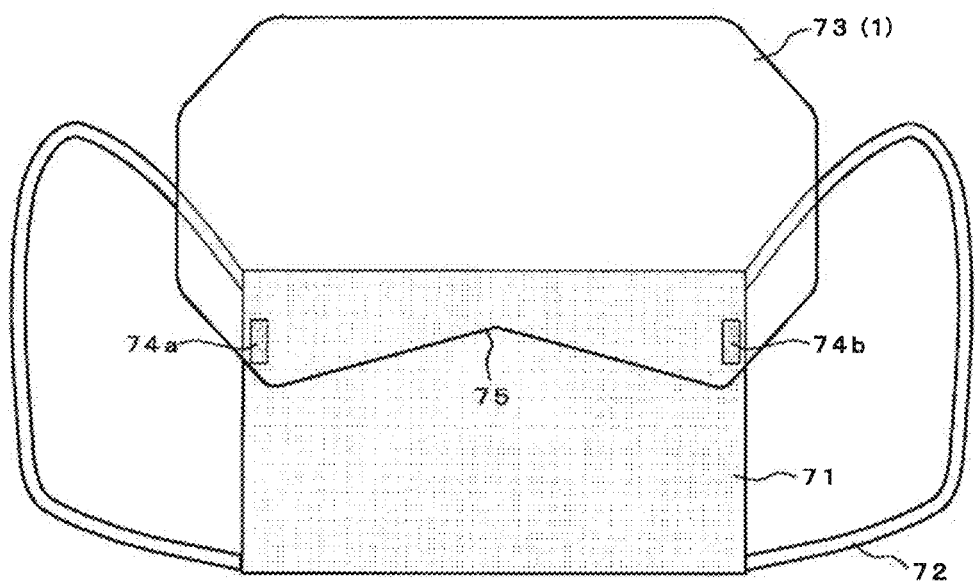
FIG. 6 is a plan view of a face protection shield according to an embodiment of the present invention.

FIG. 6 is a plan view of a face protection shield 70 in which a transparent film 1 according to the present invention is fixed as an eye shield 73 to a face mask 71. Further, FIG. 7 is a perspective view showing a state in which the face protection shield 70 shown in FIG. 6 is worn on a face.

Figure 7:
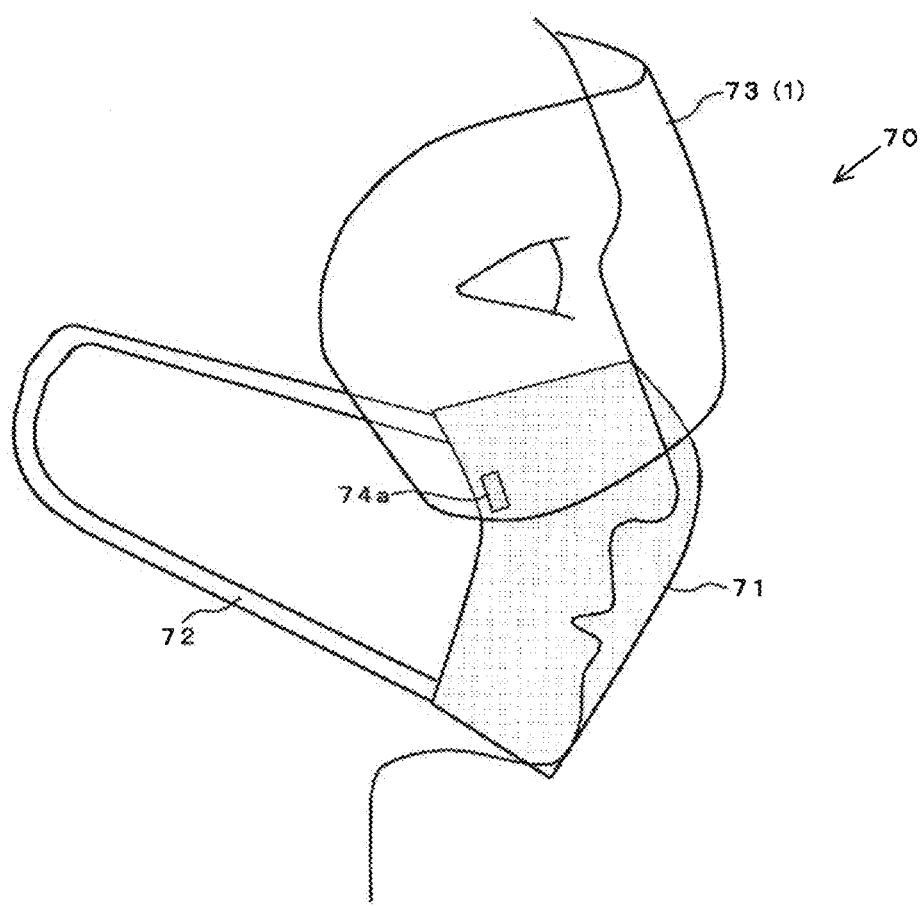
FIG. 7 is a perspective view of a state in which the face protection shield according to the embodiment is worn.

As shown in FIGS. 6 and 7, the face mask 71 covers the nose, mouth, and part of the chin of the wearer, and is held on the face with a string 72 and the like. As the face mask 71, any medical face mask can be used, and for example, a breathable mask having a multi-layer structure for preventing entering of bacteria can be used.

The eye shield 73 is formed of the transparent film 1 according to the present invention, and is fixed to the face mask 71 at joining regions 74A and 74B in order to prevent liquid and splashed matters from flying into the eyes of the wearer.

Further, the eye shield 73 has a sufficiently large width with respect to the width of the face mask 71, and has a size capable of covering the surroundings of the eyes of the wearer widely. Further, the eye shield 73 has a hollow 75 at the center of the lower side. With such a hollow 75, when the face protection shield 70 is worn on the face, the eye shield 73 curves around the nose of the wearer, and forms a curve along the face.

The joining regions 74A and 74B are provided at both left and right end portions of the face mask 71, which correspond to lateral sides of the nose when worn. As methods of fixing the eye shield 73 to the face mask 71 at the joining regions 74A and 74B, there can be used ultrasonic deposition, thermal adhesion, a mechanical joint such as a rivet, and the like. The sizes of the joining regions 74A and 74B may each be a size that can fix the eye shield 73, and can each be a width of 3 to 15 mm and a length of 5 to 30 mm, for example. With such joining regions 74A and 74B, it becomes not necessary to press the eye shield 73 against the face with the string 72, the attaching and detaching of the face protection shield 70 can be made easy and simple.

EXAMPLES

Hereinafter, the present invention will be described specifically by way of examples.

Examples 1 and 2 and Comparative Example 1

With the following steps, a transparent film was prepared, which had a transparent resin layer on which a moth-eye structure was formed on each of the both surfaces of a transparent base material, and in which the interface between the transparent resin layer and the transparent base material had a concave-convex shape (that is, the interface had undulations).

First, as shown in FIG. 2, a master for manufacturing the transparent resin layer was manufactured by the method described in WO 2012/133943, the transparent resin layer having structural bodies 21 arranged in a hexagonal lattice shape, the structural bodies 21 each having a bell shape and an elliptical base (height H1 of structural body=250 nm, pitch P1 of structural bodies within a track=230 nm, pitch P2 of structural bodies within a track=153 nm, track pitch TP=153 nm).

Further, as transparent base materials, transparent films made of resins shown in Table 1 were prepared. Note that the pitches of the concave-convex shapes of the transparent films according to Examples 1 and 2 and Comparative Example 1 were in the range of 1 to 100 mm, and the height differences were in the range of 0.1 to 9.5 μm.

Further, the refractive index (wavelength of 589 nm (sodium D line)) of each transparent base material was measured with Abbe Refractometer (manufactured by ATAGO CO., LTD.).

Several drops of a UV-curing resin composition having a hydrophilic group were dropped on the master, the transparent base material was press-adhered to the master, and the resultant was irradiated with UV. Here, used as the UV-curing resin composition having a hydrophilic group was a mixture obtained by adding, to a mixture of urethane acrylate (EBECRYL9270, manufactured by Daicel Corporation) and methoxy polyethylene glycol monomethacrylate (SR550, manufactured by Sartomer Co., Inc.) in a mass ratio of 7:3, a photopolymerization initiator IRGACURE 184 (manufactured by BASF Japan Ltd.) in an amount of 3 mass % with respect to the total mass of the UV-curing resin composition.

The UV irradiation was performed by emitting 1000 mJ of ultraviolet rays from the transparent base material side for one minute.

After the UV-curing resin was cured through the UV irradiation, the transparent film was released from the master, and the transparent film in which the transparent resin layer was formed on one surface of the transparent base material as shown in FIG. 1 was obtained. With a similar process, the transparent resin layer was also formed on another surface that faces the one surface of the transparent base material 10, and thus, the transparent film as shown in FIG. 4 was obtained, in which the transparent resin layer was formed on each of the both surfaces of the transparent base material.

The refractive index (wavelength of 589 nm (sodium D line)) of each of the transparent resin layers of the transparent films according to Examples 1 and 2 and Comparative Example 1 was measured with Abbe Refractometer (manufactured by ATAGO CO., LTD.), and was 1.53.

Comparative Example 2

With the following steps, a transparent film was prepared, in which the refractive index of the transparent resin layer was different from the refractive index of the transparent base material, and in which the interface between the transparent resin layer and the transparent base material was not a concave-convex shape but was flat.

First, several drops of a UV-curing resin were dropped on a transparent base material (PC, refractive index 1.58) similar to Example 2, a flat glass plate was pressed, and the resultant was irradiated with UV. Here, used as the UV-curing resin was a mixture obtained by adding, to a mixture of urethane acrylate (EBECRYL9270, manufactured by Daicel Corporation) and methoxy polyethylene glycol monomethacrylate (SR550, manufactured by Sartomer Co., Inc.), a photopolymerization initiator IRGACURE 184 (manufactured by BASF Japan Ltd.) in an amount of 3 wt % with respect to the total mass of the UV-curing resin composition. Note that the mixing ratio of urethane acrylate to methoxy polyethylene glycol monomethacrylate was adjusted such that the refractive index of the cured product of the UV-curing resin was 1.58.

The UV irradiation was performed by emitting 1000 mJ of ultraviolet rays from the transparent base material side for one minute. Consequently, a flat UV-cured resin layer having a refractive index similar to the refractive index of the transparent base material was obtained on the transparent base material. The height difference of the UV-cured resin layer was measured similarly as mentioned above, and the height difference was less than 0.1 μm.

Next, on the flat UV-cured resin layer, the transparent resin layer (refractive index: 1.53) was formed with a similar process as Example 1, and thus, the transparent film was obtained in which the refractive index of the transparent resin layer was different from the refractive index of the UV-cured resin layer and the transparent base material underneath, and in which the interface between the transparent resin layer and the UV-cured resin layer was not a concave-convex shape but was flat.

[Evaluation of Light Transmittance, Haze, and Visibility]

The light transmittance and haze (turbidity) of each of the transparent films according to Examples 1 and 2 and Comparative Examples 1 and 2 were measured by a haze meter (HM-150, manufactured by Murakami Color Research Laboratory).

The evaluation of visibility was performed through the following method. First, a transparent film was placed in a manner that a film surface faced the front of an observer, and white fluorescent light was placed as illumination light above a midpoint between the transparent film and the observer. Next, the illuminance of the white fluorescent light was set to 2000 lux or 500 lux, and the observer observed the transparent film. The ease of visually recognizing the transparent film by the observer (visibility) in this case was evaluated into five grades from "1", which represents that the transparent film is easily visually recognizable owing to a reflection pattern, to "5", which represents that the transparent film is not visually recognizable.

The evaluation results described above are shown in Table 1.

TABLE 1

| | Transparent base material | | | Moth-eye layer | | Transparent film | | | | |
|---|---|---|---|---|---|---|---|---|---|---|
| | Resin | Refractive index | Presence/ absence of undulations | Refractive index | Placement | Difference in refractive index between moth-eye layer and transparent base material | Transmittance | Haze (%) | Visibility* (2000 lux) | Visibility* (500 lux) |
| Example 1 | PET | 1.60 | Present | 1.53 | Both surfaces | 0.07 | 99.0 | 0.3 | 1 | 2 |
| Example 2 | PC | 1.58 | Present | 1.53 | Both surfaces | 0.05 | 99.2 | 0.2 | 2 | 3 |

TABLE 1-continued

|  | Transparent base material | | | Transparent film | | | | | |
|---|---|---|---|---|---|---|---|---|---|
|  | | | | Moth-eye layer | | Difference in refractive index between moth-eye layer | | | |
|  | Resin | Refractive index | Presence/ absence of undulations | Refractive index | Placement | and transparent base material | Transmittance | Haze (%) | Visibility* (2000 lux) | Visibility* (500 lux) |
| Comparative Example 1 | COC | 1.53 | Present | 1.53 | Both surfaces | 0 | 99.1 | 0.1 | 5 | 5 |
| Comparative Example 2 | PC | 1.58 | Absent | 1.53 | Both surfaces | 0.05 | 99.2 | 0.2 | 4 | 4 |

*Visibility:
1: Easily visually recognizable <=> 5: Not visually recognizable

Referring to the results shown in Table 1, in the case where the refractive index of the transparent base material was different from the refractive index of the transparent resin layer, and the interface between the transparent base material and the transparent resin layer had a concave-convex shape (Examples 1 and 2), it was found that the visibility of the transparent film enhanced owing to the reflection pattern. Further, it was also found that it was preferable that the difference between the refractive index of the transparent base material and the refractive index of the transparent resin layer be more than or equal to 0.05. On the other hand, in the case where the refractive index of the transparent base material was the same as the refractive index of the transparent resin layer (Comparative Example 1), and the interface between the transparent base material and the transparent resin layer was flat (Comparative Example 2), it was found that the visibility of the transparent film decreased.

Further, the transparent films according to Examples 1 and 2 were each actually cut into a size that can cover most of the field of view of the observer, and were each worn by the observer as a face protection shield in order to confirm the field of view through the transparent film. As a result, it was found that a satisfactory field of view could be obtained.

Example 3

Moreover, through the same method as Example 1, a transparent film having a transparent resin layer only on one surface of a transparent base material as shown in FIG. 1 was manufactured.

Figure 8:
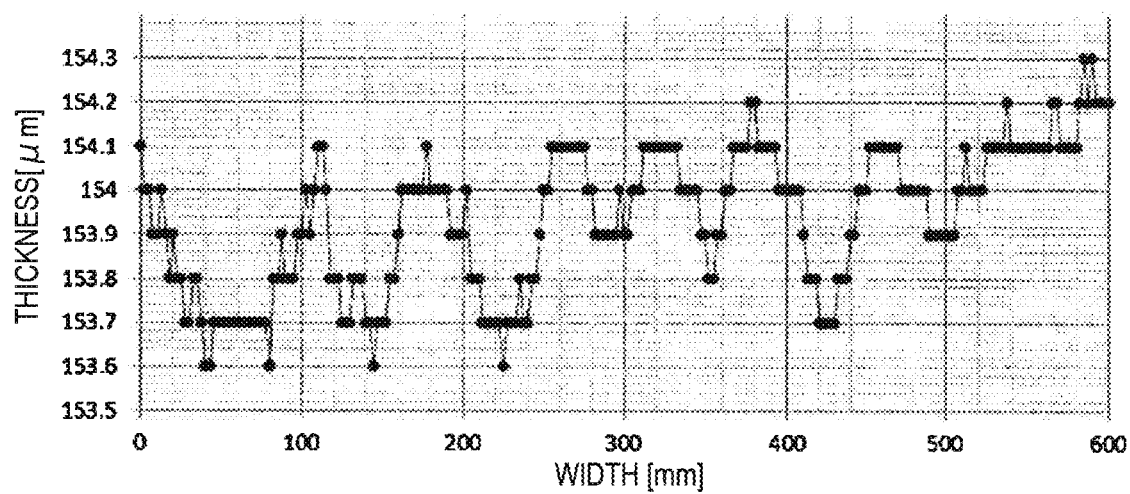
FIG. 8 is a graph which plots change in thickness of a transparent base material with respect to a film width direction in a transparent film according to Example 3.

Here, on the transparent film according to Example 3, change in thickness of the transparent base material in a film width direction was measured. To be specific, 20 or more measurement points were set within the range of 600 mm in the film width direction, and, using a digimatic measuring unit (Litematic VL-50S-B, manufactured by Mitutoyo Corporation), each measurement point was measured 10 times. FIG. 8 is a graph showing the results.

Referring to the graph shown in FIG. 8, it is found that a surface of the transparent base material included in the transparent film according to the present embodiment has a concave-convex shape. Further, it is found that the pitch of the concavities and convexities of the concave-convex shape is approximately 1 to 100 mm. Accordingly, it is found that the interface between the transparent base material and the transparent resin layer also has a similar concave-convex shape. Note that the concave-convex shape of the interface between the transparent base material and the transparent resin layer can also be measured by, in addition to the above-mentioned method, using a laser microscope or the like, for example.

The light transmittance and the haze (turbidity) of the transparent film according to Example 3 were measured in the same manner as Example 1, and the light transmittance was 94.8% and the haze was 0.3%. In addition, the visibility of the transparent film according to Example 3 was evaluated through the same method as Example 1, and the reflection pattern could be recognized and the visibility was confirmed to be enhanced. Moreover, the transparent film according to Example 3 was worn by a wearer as a face protection shield in order to allow the wearer to confirm the field of view through the transparent film, it was found that a satisfactory field of view in the same manner as Example 1 could be obtained. Accordingly, it was found that the pitch of the concave-convex shape of the interface between the transparent base material and the transparent resin layer was preferably in the range of 1 to 100 mm.

[Thickness of Basal Layer and Change in Color Tone of Transparent Film]

Moreover, studies have been made to find a degree of height difference in the concave-convex shape of the interface between the transparent base material and the transparent resin layer at which the reflection pattern is visually recognized, the reflection pattern being the color tone of the transparent film being changed into rainbow colors.

To be specific, first, a test transparent film was prepared by using a flat PET (refractive index: 1.60) film or PC (refractive index: 1.58) film as a transparent base material, and laminating, on the transparent base material, a transparent resin layer (refractive index: 1.53) on which structural bodies were formed through the same manner as Example 1. Next, in the case where the test transparent film was irradiated with white fluorescent light, the thickness of a basal layer was changed within the range of 0 to 10 m, to simulate how lightness $L^*$ and chromaticity indices $a^*$ and $b^*$ change in the $L^*a^*b^*$ color space. Note that TFCalc (manufactured by Software Spectra Inc.) was used for the simulation. The simulation results are shown in FIGS. 9A, 9B, and 9C.

Figure 9A:
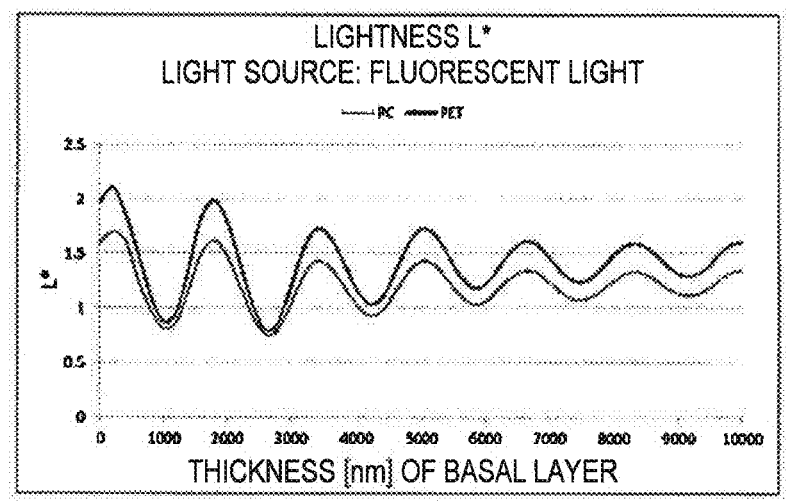
FIG. 9A is a graph showing simulation results of L* in a case where a thickness of a basal layer formed on a flat transparent base material is changed in a range of 0 to 10 μm.
Figure 9B:
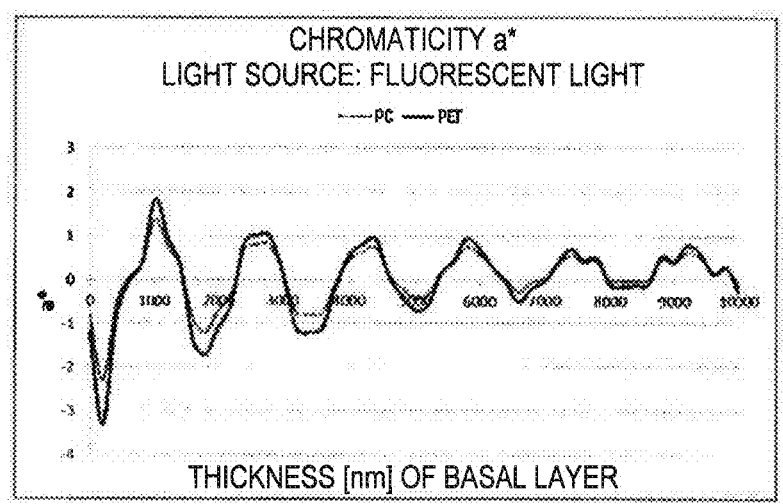
FIG. 9B is a graph showing simulation results of a* in the case where the thickness of the basal layer formed on the flat transparent base material is changed in the range of 0 to 10 μm.
Figure 9C:
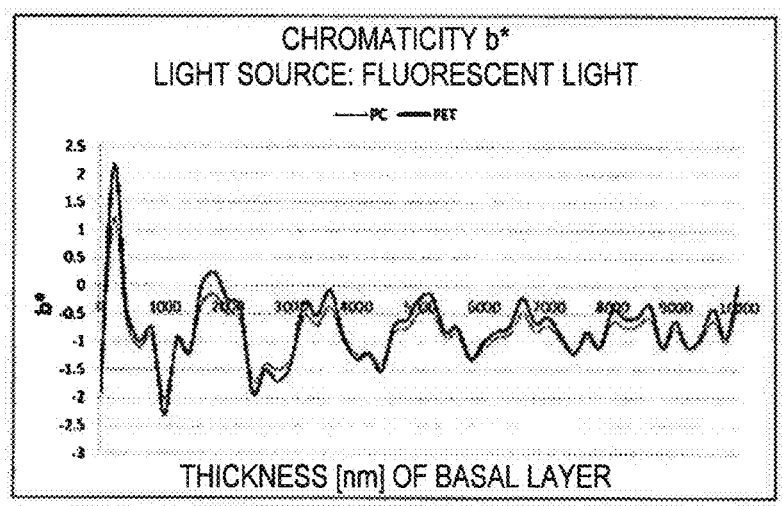
FIG. 9C is a graph showing simulation results of b* in the case where the thickness of the basal layer formed on the flat transparent base material is changed in the range of 0 to 10 μm.

Referring to the results shown in FIGS. 9A, 9B, and 9C, in the transparent film, the color tone changes periodically every approximately 1500 nm change in the thickness of the basal layer. Accordingly, it was found that, taking into account the results shown in FIGS. 9A, 9B, and 9C, when the interface between the transparent base material and the transparent resin layer had a concave-convex shape in which the thickness of the basal layer changed more than or equal to 0.1 μm, a non-wearer could visually recognize the change of the color tone of the transparent film. Therefore, it was found that the height difference between the concavities and convexities of the concave-convex shape was preferably in the range of 0.1 to 9.5 μm.

The preferred embodiment(s) of the present invention has/have been described above with reference to the accompanying drawings, whilst the present invention is not limited to the above examples. A person skilled in the art may find various alterations and modifications within the scope of the appended claims, and it should be understood that they will naturally come under the technical scope of the present invention.

REFERENCE SIGNS LIST 1, 1A, 1B, 1C, 1D transparent film for face protection
10 transparent base material
10a transparent resin sheet
10b surface treatment layer
20 transparent resin layer
21 structural body
22 basal layer
70 face protection shield
71 face mask
72 string
73 eye shield
74a, 74b joining region
75 hollow

The invention claimed is:

1. A transparent film for a face protection shield comprising:
a transparent base material having flexibility; and
a transparent resin layer laminated on at least one surface of the transparent base material, the transparent resin layer having on a surface not laminated to the transparent base material a plurality of structural bodies including concavities or convexities provided at a pitch of less than or equal to a visible light wavelength, wherein
a refractive index of the transparent base material is different from a refractive index of the transparent resin layer,
an interface between the transparent base material and the transparent resin layer has a concave-convex shape,
the transparent resin layer comprises a basal layer integrally formed with the plurality of structural bodies and in direct contact with the transparent base material, the basal layer having an average thickness of 0.5 to 10 μm, wherein the thickness of the basal layer changes in a corresponding manner to the concave-convex shape of the interface between the transparent base material and the transparent resin layer, and
wherein a pitch of the concave-convex shape of the interface between the transparent base material and the transparent resin layer is more than or equal to 100 times the pitch of the concavities or convexities of the plurality of structural bodies.

2. The transparent film for a face protection shield according to claim 1, wherein
a difference between the refractive index of the transparent base material with respect to light having a wavelength of 589 nm and the refractive index of the transparent resin layer with respect to light having a wavelength of 589 nm is more than or equal to 0.05.

3. The transparent film for a face protection shield according to claim 1, wherein
the concave-convex shape has a height difference in a range of 0.1 to 9.5 μm and a pitch in a range of 1 to 100 mm.

4. The transparent film for a face protection shield according to claim 1, wherein
each of both sides of the transparent base material is laminated with the transparent resin layer.

5. The transparent film for a face protection shield according to claim 1, wherein
the transparent resin layer is a cured product of an ultraviolet-curing resin composition having a hydrophilic functional group.

6. A face protection shield to which the transparent film for a face protection shield according to claim 1 is attached.

7. The transparent film for a face protection shield according to claim 1, wherein an average thickness of the basal layer is 0.5 μm to less than 1.5 μm and a height difference of the concave-convex shape is 0.1 to 1 μm.

8. The transparent film for a face protection shield according to claim 1, wherein an average thickness of the basal layer is more than or equal to 1.5 μm and less than 5 μm and a height difference of the concave-convex shape is 0.1 μm to 4.5 μm.

9. The transparent film for a face protection shield according to claim 1, wherein an average thickness of the basal layer is more than or equal to 5 μm and less than or equal to 10 μm and a height difference of the concave-convex shape is 0.1 to 9.5 μm.

10. The transparent film for a face protection shield according to claim 1, wherein the pitch of the concave-convex shape of the interface between the transparent base material and the transparent resin layer is within a range of from 1 to 100 mm.

11. The transparent film for a face protection shield according to claim 10, wherein the pitch of the concave-convex shape of the interface between the transparent base material and the transparent resin layer is within a range of from 2.5 to 50 mm.

* * * * *